(12) United States Patent
Baughman et al.

(10) Patent No.: US 10,743,805 B2
(45) Date of Patent: *Aug. 18, 2020

(54) HAPTIC INTERFACE FOR GENERATING PREFLEX STIMULATION

(71) Applicant: International Business Machines Corporation, Armonk, NY (US)

(72) Inventors: Aaron K. Baughman, Silver Spring, MD (US); Diwesh Pandey, Bangalore (IN); John P. Perrino, Hedgesville, WV (US); Todd R. Whitman, Bethany, CT (US)

(73) Assignee: International Business Machines Corporation, Armonk, NY (US)

( * ) Notice: Subject to any disclaimer, the term of this patent is extended or adjusted under 35 U.S.C. 154(b) by 545 days.

This patent is subject to a terminal disclaimer.

(21) Appl. No.: 15/612,403

(22) Filed: Jun. 2, 2017

(65) Prior Publication Data

US 2018/0344232 A1   Dec. 6, 2018

(51) Int. Cl.
  *A61B 5/16*   (2006.01)
  *A61B 5/00*   (2006.01)
  *A61B 5/11*   (2006.01)
  *G06N 5/02*   (2006.01)

(52) U.S. Cl.
  CPC ............ *A61B 5/162* (2013.01); *A61B 5/0051* (2013.01); *A61B 5/1104* (2013.01); *A61B 5/1118* (2013.01); *G06N 5/022* (2013.01); *A61B 5/0022* (2013.01); *A61B 5/11* (2013.01); *A61B 5/7267* (2013.01); *A61B 2503/10* (2013.01)

(58) Field of Classification Search
  CPC ..... A61B 5/162; A61B 5/1104; A61B 5/1118; A61B 5/0051; A61B 5/11; A61B 2503/10; A61B 5/7267; G06N 5/022
  See application file for complete search history.

(56) References Cited

U.S. PATENT DOCUMENTS

| | | |
|---|---|---|
| 6,788,976 B2 | 9/2004 | Gesotti |
| 8,565,888 B2 | 10/2013 | Buhlmann et al. |
| 8,725,265 B2 | 5/2014 | Schauer et al. |

(Continued)

FOREIGN PATENT DOCUMENTS

| | | |
|---|---|---|
| CN | 102341766 B | 9/2014 |
| EP | 2165733 A1 | 3/2010 |

OTHER PUBLICATIONS

Golshan et al., "A Multiple Kernel Learning Approach for Human Behavioral Task Classification using STN-LFP Signal", ResearchGate, Artile, Jul. 2016, 5 pages.

(Continued)

*Primary Examiner* — Sean P Dougherty
(74) *Attorney, Agent, or Firm* — Edward J. Wixted, III

(57) ABSTRACT

In an approach to generating preflex stimulation, one or more computer processors monitor one or more sensing devices for data associated with a user activity. Based, at least in part, on the data associated with the user activity, the one or more computer processors predict a user reaction associated with the user activity. The one or more computer processors transmit a preflex stimulus to at least one muscle of the user, wherein the at least one muscle is associated with the user reaction. The one or more computer processors determine a reaction time of the at least one muscle to the preflex stimulus.

17 Claims, 6 Drawing Sheets

(56) References Cited

U.S. PATENT DOCUMENTS

| | | |
|---|---|---|
| 8,775,340 B2 | 7/2014 | Waxman et al. |
| 9,293,015 B2 | 3/2016 | Mar et al. |
| 2009/0209878 A1 | 8/2009 | Sanger |
| 2010/0249637 A1 | 9/2010 | Walter |
| 2013/0204097 A1* | 8/2013 | Rondoni ............ A61B 5/04001 600/301 |
| 2013/0261423 A1 | 10/2013 | Herrala et al. |
| 2014/0272839 A1 | 9/2014 | Cutler |
| 2014/0364678 A1 | 12/2014 | Harry et al. |
| 2015/0173430 A1 | 6/2015 | Langer et al. |
| 2015/0375044 A1 | 12/2015 | Molyneux et al. |
| 2016/0038073 A1* | 2/2016 | Brown ............. A61M 16/0443 600/301 |
| 2016/0106344 A1* | 4/2016 | Nazari .................... A61B 5/11 600/301 |
| 2016/0231814 A1 | 8/2016 | Grant et al. |
| 2017/0061817 A1 | 3/2017 | May |
| 2017/0124474 A1 | 5/2017 | Kashyap |
| 2017/0168773 A1 | 6/2017 | Keller |
| 2018/0140503 A1 | 5/2018 | Kim |
| 2018/0279934 A1* | 10/2018 | Wo ........................ G16H 10/20 |

OTHER PUBLICATIONS

Gueugneau et al., "High-frequency neuromuscular electrical stimulation modulates 2 interhemispheric inhibition in healthy Humans", Articles in PresS. J Neurophysiol, Nov. 9, 2016, 36 pages.

Murer et al., "TorqueScreen: Actuated Flywheels for Ungrounded Kinesthetic Feedback in Handheld Devices", Cool New Stuff, TEI 2015, Jan. 15-19, 2015, 4 pages.

Mell et al., "The NIST Definition of Cloud Computing", National Institute of Standards and Technology, U.S. Department of Commerce, NIST Special Publication 800-145, Sep. 2011, 7 pages.

U.S. Appl. No. 15/612,403, filed Dec. 29, 2017.

List of IBM Patents or Patent Applications Treated as Related. Filed Herewith. 2 pages.

* cited by examiner

HAPTIC INTERFACE FOR GENERATING PREFLEX STIMULATION

BACKGROUND OF THE INVENTION

The present invention relates generally to the field of tactile signaling systems, and more particularly to a haptic analytic interface for determining and generating preflex stimulation.

A haptic analytic interface is a system that interfaces with a haptic device enabling a human to interact with a computer through bodily sensations and movements. Haptics refers to a type of human-computer interaction technology that encompasses tactile feedback or other bodily sensations to perform actions or processes on a computing device.

Muscle spindles are sensory receptors within a muscle that primarily detect changes in the length of the muscle. They convey length information to the central nervous system via sensory neurons. The brain can process this information to determine the position of body parts. The responses of muscle spindles to changes in length also play an important role in regulating the contraction of muscles, by activating motor neurons via the stretch reflex to resist muscle stretch. Muscle spindles are embedded in extrafusal muscle fibers. Preflexes are the zero-delay, intrinsic response of a neuromusculoskeletal system to perturbation that auto-stabilize movements using the nonlinear visco-elastic properties of muscles when they contract.

Proprioception is the sense of the relative position of neighboring parts of the body and strength of effort being employed in movement. In humans, it may be provided by proprioceptors (muscle spindles) in skeletal striated muscles. The initiation of proprioception is the activation of a proprioceptor in the periphery. The proprioceptive sense is believed to be composed of information from sensory neurons located in the inner ear (motion and orientation) and in the stretch receptors located in the muscles and the joint-supporting ligaments (stance). Proprioceptors, sometimes known as adequate stimuli receptors, are sensory receptors that receives stimuli from within the body, especially in response to position and movement.

SUMMARY

Embodiments of the present invention disclose a method, a computer program product, and a system for generating preflex stimulation. The method may include one or more computer processors monitoring one or more sensing devices for data associated with a user activity. Based, at least in part, on the data associated with the user activity, the one or more computer processors predict a user reaction associated with the user activity. The one or more computer processors transmit a preflex stimulus to at least one muscle of the user, wherein the at least one muscle is associated with the user reaction. The one or more computer processors determine a reaction time of the at least one muscle to the preflex stimulus.

DETAILED DESCRIPTION

Human preflexes are generated to induce movement before an event occurs. Within sports, for example, a player may feel the proprioceptors (i.e., muscle spindles), stimulated and moved in a particular direction in anticipation of the player's next move. Embodiments of the present invention recognize that athletic performance, or any activity requiring a quick, muscular reaction, may be improved by providing a haptic analytic interface which, through machine learning, can stimulate muscles in anticipation of needed movements and coerce a user into movement. Embodiments of the present invention also recognize that by monitoring preflex reaction time to a stimulus, overstimulation can be avoided, effectiveness of the stimulation can be measured, and preflex reaction times can be maintained around optimal levels for the user. Implementation of embodiments of the invention may take a variety of forms, and exemplary implementation details are discussed subsequently with reference to the Figures.

Figure 1:
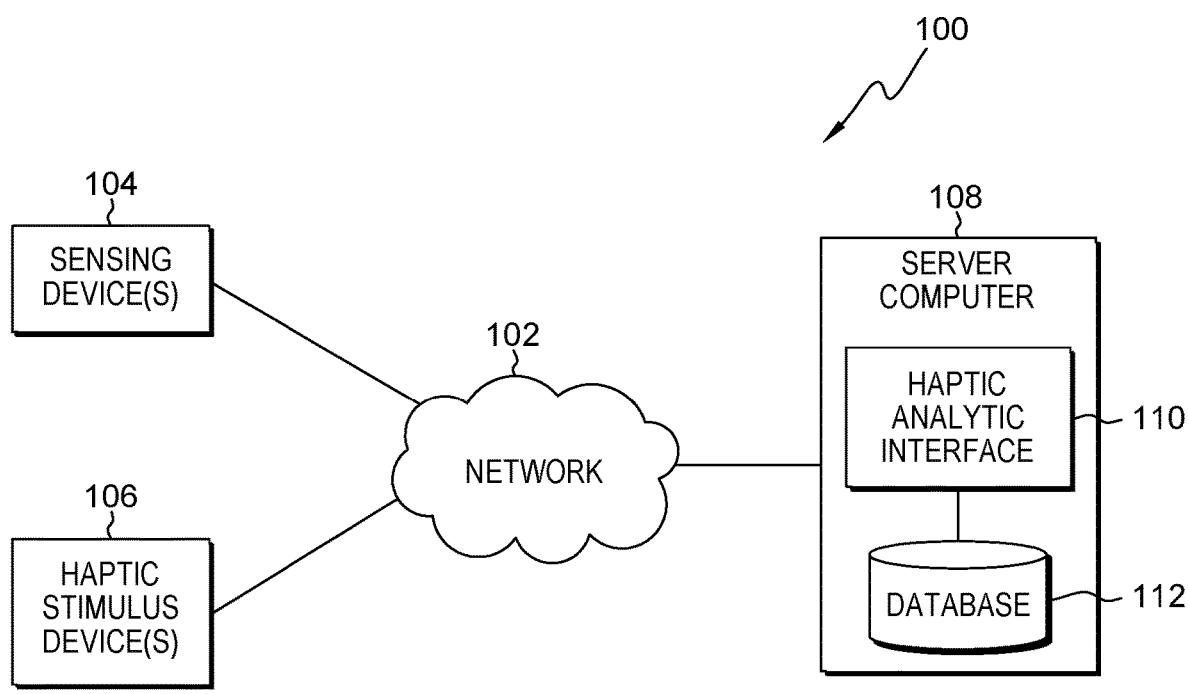
FIG. 1 is a functional block diagram illustrating a distributed data processing environment, in accordance with an embodiment of the present invention.

FIG. 1 is a functional block diagram illustrating a distributed data processing environment, generally designated 100, in accordance with one embodiment of the present invention. The term "distributed" as used herein describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Distributed data processing environment 100 includes sensing device(s) 104, haptic stimulus device(s) 106, and server computer 108, all interconnected over network 102. Network 102 can be, for example, a telecommunications network, a local area network (LAN), a wide area network (WAN), such as the Internet, or a combination of the three, and can include wired, wireless, or fiber optic connections. Network 102 can include one or more wired and/or wireless networks that are capable of receiving and transmitting data, voice, and/or video signals, including multimedia signals that include voice, data, and video information. In general, network 102 can be any combination of connections and protocols that will support communications between sensing device(s) 104, haptic stimulus device(s) 106, server computer 108, and other computing devices (not shown) within distributed data processing environment 100.

Sensing device(s) 104 can be one or more of a plurality of devices known in the art which detect or measure a physical property and then record or otherwise respond to that property, such as vibration, chemicals, radio frequencies, environment, weather, humidity, light, etc. In an embodiment, sensing device(s) 104 may be external devices which are included in the Internet of Things (IoT), connected to server computer 108 via network 102. For example, sensing device(s) 104 may be a laser or sonar device in a venue which can measure speed or position. In an embodiment, sensing device(s) 104 may be a wearable device, such as a camera or a pair of augmented reality glasses. In a further embodiment, sensing device(s) 104 may be one or more wearable devices that monitor physiological states of the user, via biometric readings, such as heart rate, blood pressure, respiration, etc. In yet another embodiment, sensing device(s) 104 may detect fatigue in the user. In an embodiment, sensing device(s) 104 can track the position of the user. In another embodiment, sensing device(s) 104 can track the position of an object coming toward the user, such as a ball or a person. In one embodiment, sensing device(s) 104 may coordinate with each other for data collection.

Haptic stimulus device(s) 106 are one or more of a plurality of devices known in the art for stimulating muscle spindles. Haptic stimulus device(s) 106 may use an electric impulse on the skin in direct proximity to the muscles to be stimulated to elicit muscle contraction. Haptic stimulus device(s) 106 may also use a vibratory impulse on the skin to stimulate a muscle spindle. In one embodiment, haptic stimulus device(s) 106 are embedded in clothing or garments worn by the user such that stimulus can be delivered directly to a targeted muscle, such as in arms, legs, abdomen, etc. In one embodiment, haptic stimulus device(s) 106 may be smart devices which can determine a response to a stimulus in addition to providing the stimulus. For example, haptic stimulus device(s) 106 can determine when a muscle reacts to a stimulus by, for example, detecting when the muscle contracts.

Server computer 108 can be a standalone computing device, a management server, a web server, a mobile computing device, or any other electronic device or computing system capable of receiving, sending, and processing data. In other embodiments, server computer 108 can represent a server computing system utilizing multiple computers as a server system, such as in a cloud computing environment. In another embodiment, server computer 108 can be a laptop computer, a tablet computer, a netbook computer, a personal computer (PC), a desktop computer, a personal digital assistant (PDA), a smart phone, or any programmable electronic device capable of communicating with sensing device(s) 104, haptic stimulus device(s) 106, and other computing devices (not shown) within distributed data processing environment 100 via network 102. In another embodiment, server computer 108 represents a computing system utilizing clustered computers and components (e.g., database server computers, application server computers, etc.) that act as a single pool of seamless resources when accessed within distributed data processing environment 100. Server computer 108 includes haptic analytic interface 110 and database 112. Server computer 108 may include internal and external hardware components, as depicted and described in further detail with respect to FIG. 4.

Haptic analytic interface 110 provides a preflex stimulus to muscle spindles to generate user muscle movement in anticipation of an action or reaction during an activity in which a user is involved. Haptic analytic interface 110 also measures and learns the effectiveness of the preflex stimulation. Haptic analytic interface 110 monitors sensing device(s) 104 and predicts a reaction. Haptic analytic interface 110 transmits the preflex stimulus via haptic stimulus device(s) 106 and determines the muscle reaction time. If haptic analytic interface 110 determines that the reaction time indicates overstimulation of a muscle, then haptic analytic interface 110 modifies the stimulus. Haptic analytic interface 110 uses machine learning techniques to compare sensor data and stimulus data to available, previously generated data to determine pressure situations for the user and prioritize stimulus reaction, in order to improve the performance of the user. Haptic analytic interface 110 is depicted and described in further detail with respect to FIG. 2 and FIG. 3.

Database 112 is a repository for data used by haptic analytic interface 110. In the depicted embodiment, database 112 resides on server computer 108. In another embodiment, database 112 may reside elsewhere within distributed data processing environment 100 provided haptic analytic interface 110 has access to database 112. A database is an organized collection of data. Database 112 can be implemented with any type of storage device capable of storing data and configuration files that can be accessed and utilized by server computer 108, such as a database server, a hard disk drive, or a flash memory. Database 112 stores data and statistics associated with actions and movements of a user of sensing device(s) 104. Database 112 may also store data associated with reaction time to various stimuli from haptic stimulus device(s) 106.

Figure 2:
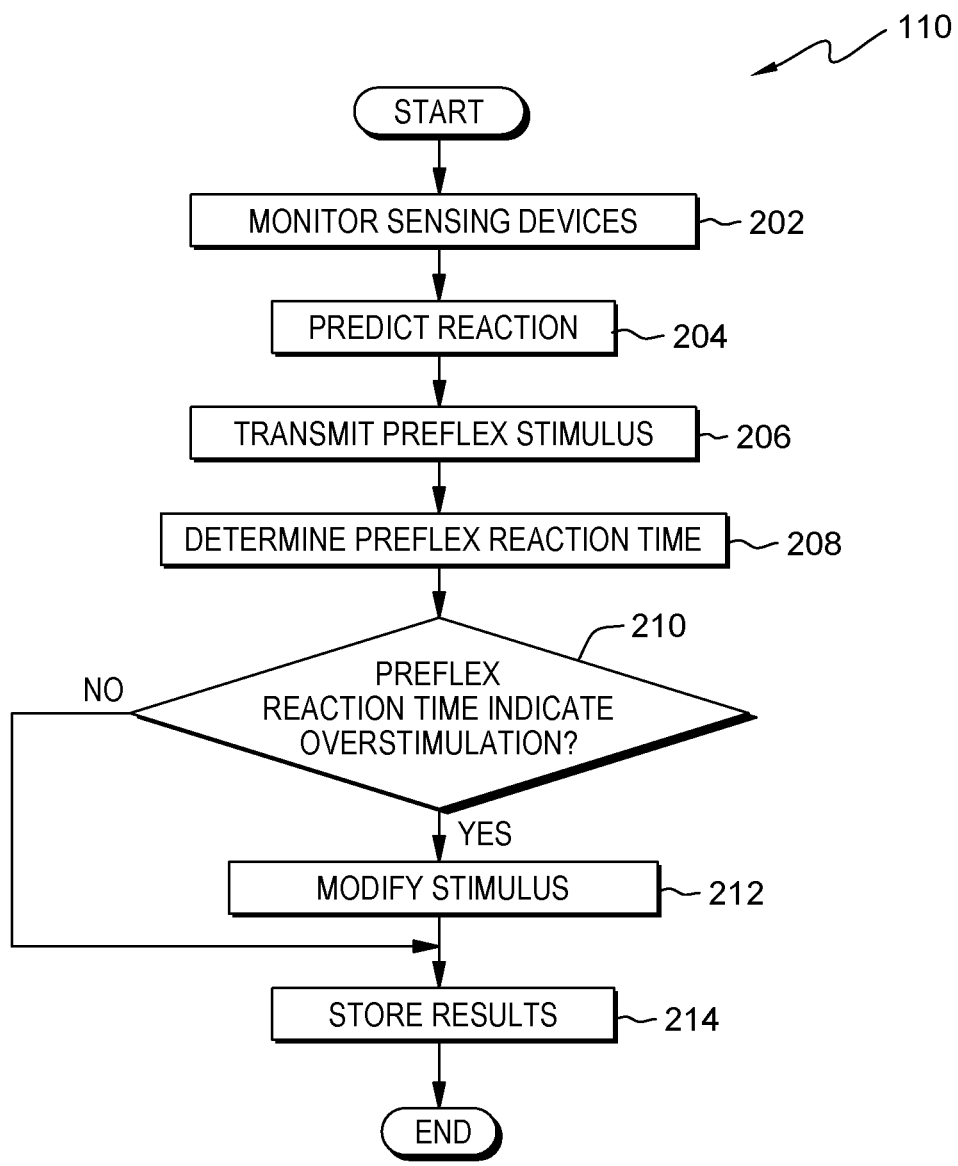
FIG. 2 is a flowchart depicting operational steps of a haptic analytic interface, on a server computer within the distributed data processing environment of FIG. 1, for stimulating muscles in anticipation of an action, in accordance with an embodiment of the present invention.

FIG. 2 is a flowchart depicting operational steps of haptic analytic interface 110, on server computer 108 within distributed data processing environment 100 of FIG. 1, for stimulating muscles in anticipation of an action, in accordance with an embodiment of the present invention.

Haptic analytic interface 110 monitors sensing device(s) 104 (step 202). While a user is involved in a physical activity, haptic analytic interface 110 monitors sensing device(s) 104 for data associated with the activity in order to predict when an action or reaction by the user is needed for the activity. In an embodiment, sensing device(s) 104 includes a tracking device which can track the location of an object moving toward the user or an object the user moves toward. For example, if the user is playing tennis, sensing device(s) 104 may include a camera that follows the motion of the ball while in play. In another example, if the user is playing basketball, sensing device(s) 104 may track the user's proximity to the basket. In an embodiment where sensing device(s) 104 include physiological sensors, haptic analytic interface 110 may also monitor the user's physical state, such as heart rate and respiration.

Haptic analytic interface 110 predicts a reaction (step 204). Based on the data received from sensing device(s) 104, haptic analytic interface 110 predicts a physical reaction the user is required to make as part of the activity and which one or more muscles will be involved in the reaction. In one embodiment, haptic analytic interface 110 determines which muscles will be involved in the reaction based on data from a previous activity stored in database 112. As will be discussed with respect to FIG. 3, machine learning enables haptic analytic interface 110 to "remember" activity outcomes and use that data to influence future activity performance. In another embodiment, haptic analytic interface 110 determines which muscles will be involved in the reaction based on data from earlier in the current activity. In a further embodiment, haptic analytic interface 110 determines which muscles will be involved in the reaction based on stored data regarding the current activity, for example, rules of play and game strategy. In one embodiment, haptic analytic interface 110 predicts at what time or in what duration of time the user will be required to react. In another embodiment, haptic analytic interface 110 predicts a location where the user will be required to react. Using the tennis example, haptic analytic interface 110, having knowledge of the game of tennis and the user's past performance, predicts the moment and location a tennis ball will arrive on the user's side of the court, after being hit by the user's opponent, and subsequently predicts a user movement required to put the user in a position to hit the ball. In another example, if the user is a firefighter, haptic analytic interface 110 may predict when the firefighter will have to move to avoid a falling beam in a burning structure by analyzing the integrity of the structure and determining where and when the beam will fall.

Haptic analytic interface 110 transmits a preflex stimulus (step 206). Based on the predicted reaction, haptic analytic interface 110 determines which one or more muscles to stimulate and transmits a preflex stimulus to the targeted muscles using haptic stimulus device(s) 106, which are in contact with the targeted muscles. The preflex stimulus enables the user to improve performance, i.e., muscle reaction time, by receiving early notice of predicted response movements.

Haptic analytic interface 110 determines the preflex reaction time (step 208). Haptic analytic interface 110 measures the time between the transmission of the preflex stimulus and the actual reaction time, for example, contraction, of the muscle. In one embodiment, haptic analytic interface 110 receives the reaction time from haptic stimulus device(s) 106. In one embodiment, haptic analytic interface 110 stores the determined reaction time in database 112.

Haptic analytic interface 110 determines whether the preflex reaction time indicates overstimulation (decision block 210). Overstimulation of a muscle may induce numbness which may, in turn, increase reaction time of the muscle to the preflex stimulus over a previously determined reaction time. Haptic analytic interface 110 trends the preflex reaction time to ensure the stimulus is not wearing off due to overstimulation. In one embodiment, haptic analytic interface 110 may compare a current preflex reaction time to historic preflex reaction times of the user stored in database 112. In another embodiment, haptic analytic interface 110 may compare the current preflex reaction time to a preflex reaction time determined earlier in the current activity.

If haptic analytic interface 110 determines the preflex reaction time indicates overstimulation ("yes" branch, decision block 210), then haptic analytic interface 110 modifies the stimulus (step 212). In response to determining that stimulated muscles are not reacting at an expected rate, haptic analytic interface 110 modifies the level of the stimulus delivered by haptic stimulus device(s) 106. For example, if haptic stimulus device(s) 106 use a vibratory impulse on the skin to stimulate a muscle spindle, haptic analytic interface 110 may reduce or dampen the frequency of the vibration. In an embodiment where the activity is a sport, if haptic analytic interface 110 determines the user is winning or ahead in a game, then haptic analytic interface 110 may reduce or re-prioritize the preflex stimuli, thereby not unnecessarily overstimulating the user's muscles.

Responsive to modifying the stimulus, or if haptic analytic interface 110 determines the preflex reaction time does not indicate overstimulation ("no" branch, decision block 210), then haptic analytic interface 110 stores the results (step 214). In order to facilitate continual learning of muscle reaction times and stimulus responses of the user in various situations, haptic analytic interface 110 stores the results in database 112. Results may include, but are not limited to, preflex reaction time, stimulus characteristics, such as frequency, and physiological state of the user at the time the stimulus was applied. In addition, results may include metadata associated with the activity, for example, date and time of the activity, weather during the activity, weight of the user, identification of an opponent, etc.

Figure 3:
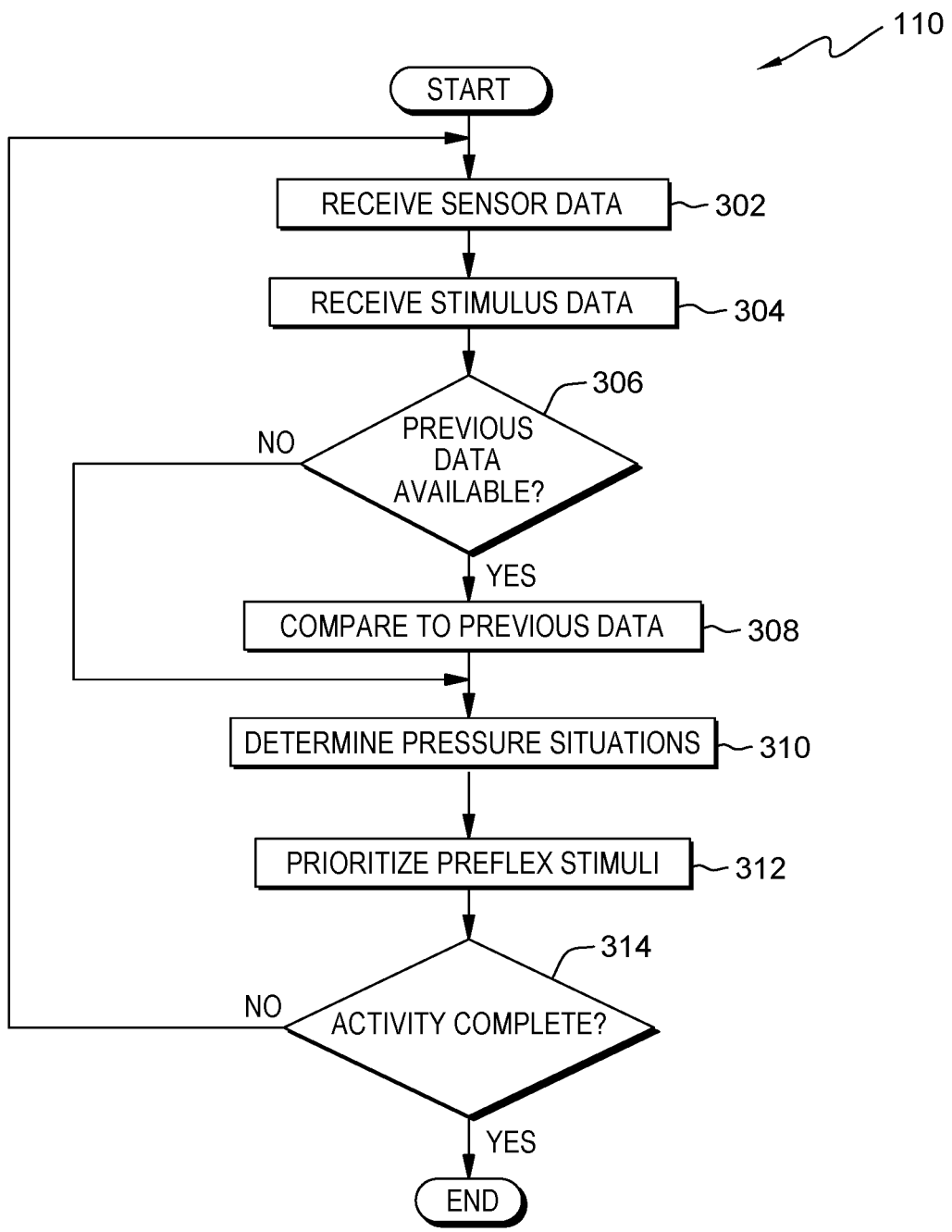
FIG. 3 is a flowchart depicting operational steps of the haptic analytic interface, on the server computer within the distributed data processing environment of FIG. 1, for learning to anticipate a need for muscle stimulus, in accordance with an embodiment of the present invention.

FIG. 3 is a flowchart depicting operational steps of haptic analytic interface 110, on server computer 108 within distributed data processing environment 100 of FIG. 1, for learning to anticipate a need for muscle stimulus, in accordance with an embodiment of the present invention.

Haptic analytic interface 110 receives sensor data (step 302). During an activity in which the user is involved, haptic analytic interface 110 receives data from sensing device(s) 104. As discussed with respect to step 202 of FIG. 2, sensing device(s) 104 sense a plurality of data associated with the user's activity. Sensing device(s) 104 may track an object moving toward or away from the user. Sensing device(s) 104 may also track the user's physiological state using various biometric readings. Sensing device(s) 104 may also track scoring of a game the user is playing as well as identification of the user's opponent(s). Haptic analytic interface 110 receives the data generated by sensing device(s) 104 during the activity.

Haptic analytic interface 110 receives stimulus data (step 304). As discussed with respect to step 206 of FIG. 2, haptic analytic interface 110 transmits preflex stimuli, via haptic stimulus device(s) 106, to the user's muscles during an activity in anticipation of an action or reaction by the user. Haptic analytic interface 110 receives data generated by haptic stimulus device(s) 106 regarding the type and duration of the stimulus. Haptic analytic interface 110 may also receive data associated with the muscle reaction time to the stimulus, as discussed with respect to step 208 of FIG. 2.

Haptic analytic interface 110 determines whether data from a previous activity is available (decision block 306). Haptic analytic interface 110 searches database 112 to determine whether any sensor or stimulus data associated with a previous activity is stored. In an embodiment, haptic analytic interface 110 determines whether data from earlier in the current activity is available.

If haptic analytic interface 110 determines data from a previous activity is available ("yes" branch, decision block 306), then haptic analytic interface 110 compares current data to previous data (step 308). Machine learning enables haptic analytic interface 110 to "remember" activity outcomes and use that data to influence future activity performance. By comparing data from a previous activity to the data from a current activity, haptic analytic interface 110 can predict the user's response to a similar situation. For example, if data from a previous activity indicates that the user's muscles were overstimulated by a particular vibratory frequency, then haptic analytic interface 110 can modify the stimulus in the current activity to prevent a similar occurrence.

Haptic analytic interface 110 determines pressure situations (step 310). Haptic analytic interface 110 combines the received sensor data and stimulus data to discover whether the user is in one or more pressure situations. In one embodiment, haptic analytic interface 110 may determine the user is in a pressure situation based on having knowledge of the activity, such as rules of play and game strategy, and data associated with the user's past performance in the activity. For example, if the user is playing hockey, haptic analytic interface 110 may combine the sensor data, tracking the user's rate of change of proximity to the goal and an increased heart rate, to determine that the user is getting ready to shoot the puck, and therefore is in a pressure situation. In the embodiment where data from a previous activity is available, haptic analytic interface 110 may also combine the previous data with the current data to determine whether the user is in a pressure situation.

Haptic analytic interface 110 prioritizes preflex stimuli (step 312). Based on the determined pressure situation, haptic analytic interface 110 determines a priority of muscle reactions to stimulate. In one embodiment, haptic analytic interface 110 uses a multi-objective optimization algorithm to determine the timing and extent of various preflex muscle stimulations to transmit in order to best react to the current situation. As would be recognized by one skilled in the art, multi-objective optimization is an area of multiple criteria decision making that is concerned with mathematical optimization problems involving more than one objective function to be optimized simultaneously. Using the hockey example, haptic analytic interface 110 may prioritize stimulation to the user's arms over the player's legs in order to slow the user's skating speed and ready the user's arm muscles to take a shot at the goal.

Haptic analytic interface 110 determines whether the current activity is complete (decision block 314). In one embodiment, haptic analytic interface 110 determines the activity is complete by monitoring sensing device(s) 104 for a change in the activity. For example, haptic analytic interface 110 may determine motion in the activity has stopped, either by the user or by activity around the user. In another example, haptic analytic interface 110 may determine that the user's heart rate has returned to a resting heart rate. If haptic analytic interface 110 determines the current activity is not complete ("no" branch, decision block 314), then haptic analytic interface 110 returns to step 302. As part of a continual learning process, haptic analytic interface 110 returns to step 302 to gather additional data while the activity is ongoing.

If haptic analytic interface 110 determines the current activity is complete ("yes" branch, decision block 314), then haptic analytic interface 110 ends.

Although described separately, in various embodiments, the actions taken by haptic analytic interface 110 as described with respect to FIG. 2 and the actions taken by haptic analytic interface 110 as described with respect to FIG. 3 may occur simultaneously, enabling cognitive machine learning with respect to preflex stimulation as a user participates in an activity.

Figure 4:
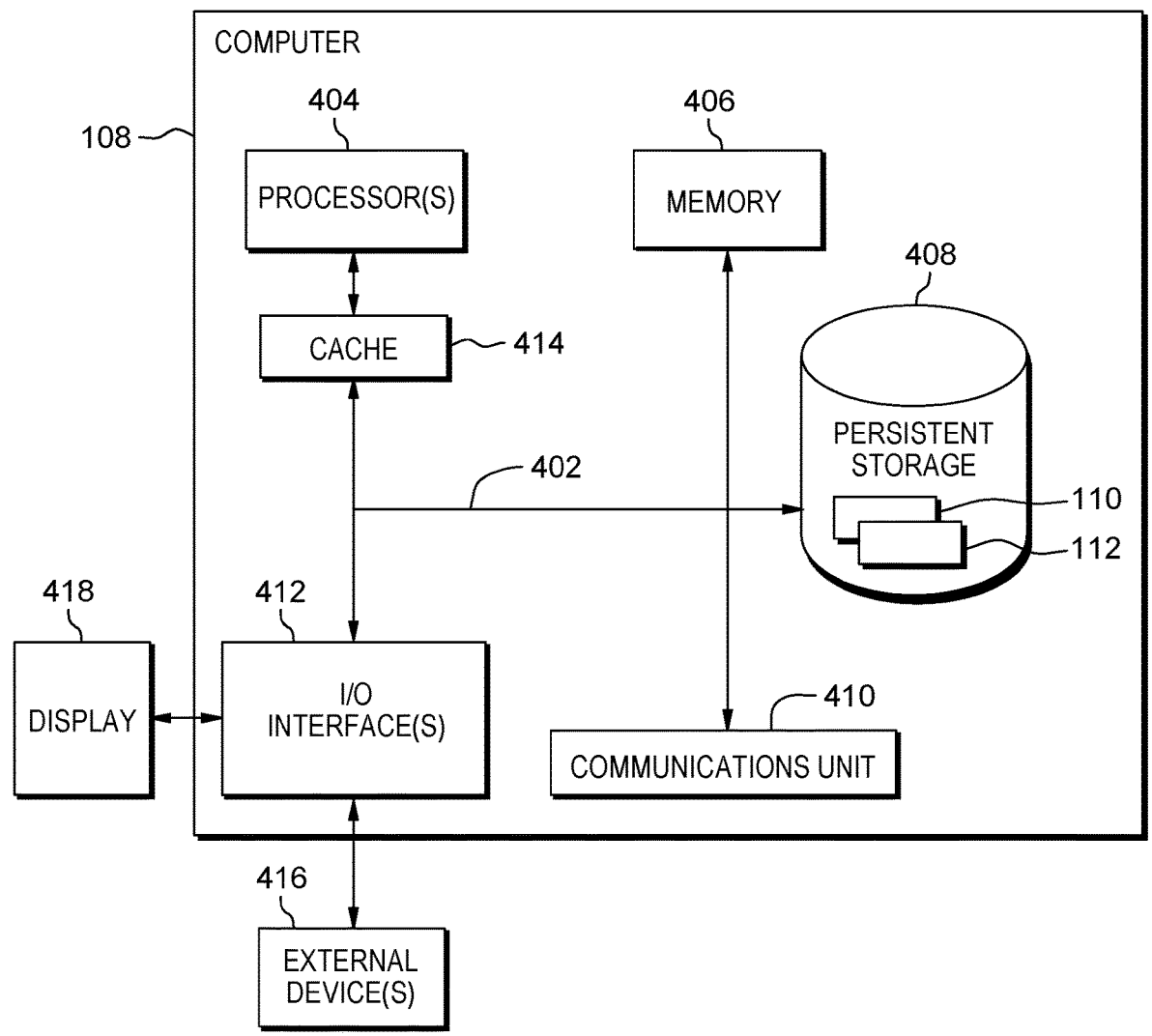
FIG. 4 depicts a block diagram of components of the server computer executing the haptic analytic interface within the distributed data processing environment of FIG. 1, in accordance with an embodiment of the present invention.

FIG. 4 depicts a block diagram of components of server computer 108 within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

Server computer 108 can include processor(s) 404, cache 414, memory 406, persistent storage 408, communications unit 410, input/output (I/O) interface(s) 412 and communications fabric 402. Communications fabric 402 provides communications between cache 414, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses.

Memory 406 and persistent storage 408 are computer readable storage media. In this embodiment, memory 406 includes random access memory (RAM). In general, memory 406 can include any suitable volatile or non-volatile computer readable storage media. Cache 414 is a fast memory that enhances the performance of processor(s) 404 by holding recently accessed data, and data near recently accessed data, from memory 406.

Program instructions and data used to practice embodiments of the present invention, e.g., haptic analytic interface 110 and database 112, can be stored in persistent storage 408 for execution and/or access by one or more of the respective processor(s) 404 of server computer 108 via memory 406. In this embodiment, persistent storage 408 includes a magnetic hard disk drive. Alternatively, or in addition to a magnetic hard disk drive, persistent storage 408 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices, including resources of sensing device(s) 104 and haptic stimulus device(s) 106. In these examples, communications unit 410 includes one or more network interface cards. Communications unit 410 may provide communications through the use of either or both physical and wireless communications links. Haptic analytic interface 110 and database 112 may be downloaded to persistent storage 408 of server computer 108 through communications unit 410.

I/O interface(s) 412 allows for input and output of data with other devices that may be connected to server computer 108. For example, I/O interface(s) 412 may provide a connection to external device(s) 416 such as a keyboard, a keypad, a touch screen, a microphone, a digital camera, and/or some other suitable input device. External device(s) 416 can also include portable computer readable storage media such as, for example, thumb drives, portable optical or magnetic disks, and memory cards. Software and data used to practice embodiments of the present invention, e.g., haptic analytic interface 110 and database 112 on server computer 108, can be stored on such portable computer readable storage media and can be loaded onto persistent storage 408 via I/O interface(s) 412. I/O interface(s) 412 also connect to a display 418.

Display 418 provides a mechanism to display data to a user and may be, for example, a computer monitor or the lenses of a head mounted display. Display 418 can also function as a touchscreen, such as a display of a tablet computer.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
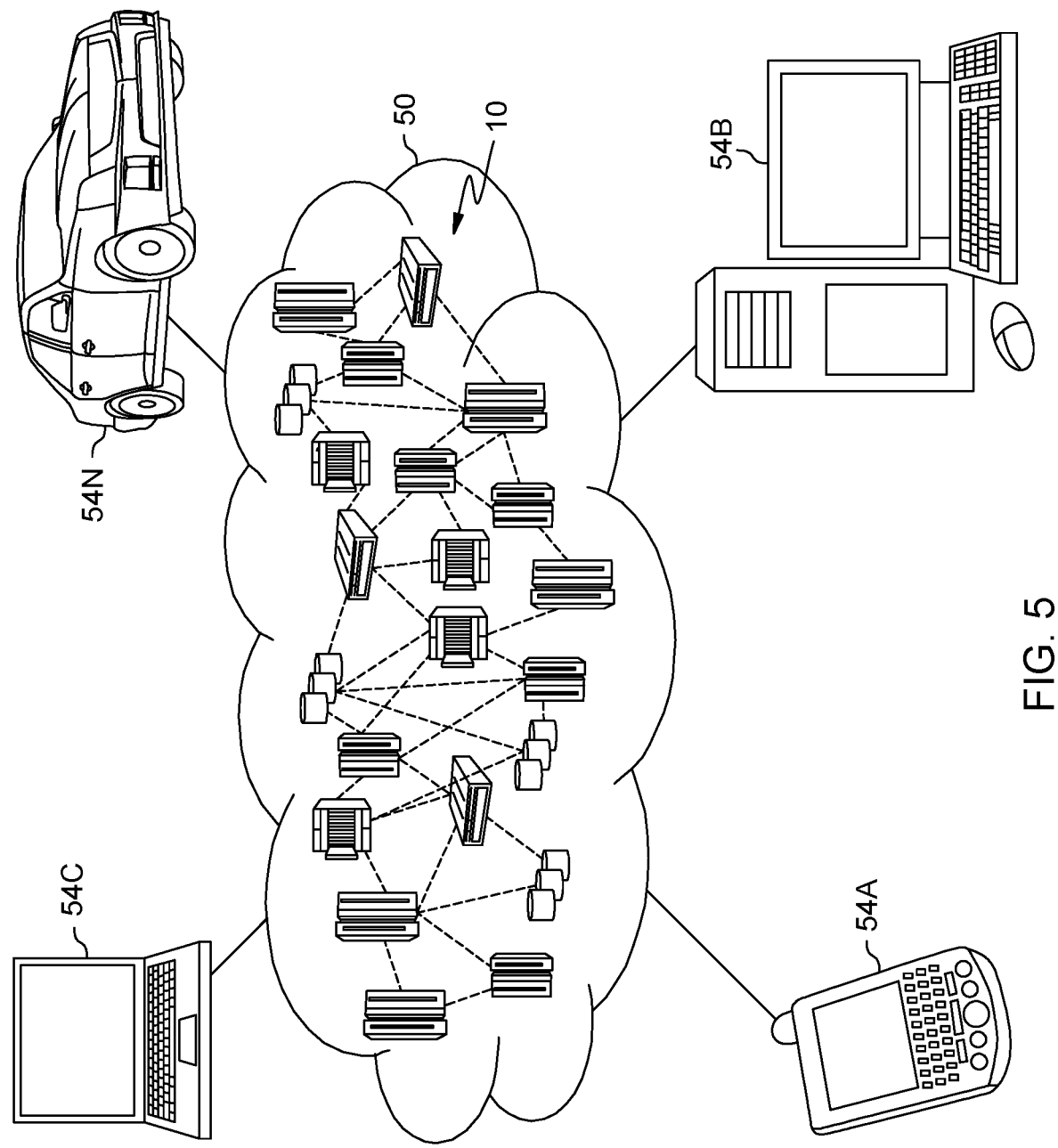
FIG. 5 depicts a cloud computing environment in accordance with an embodiment of the present invention.

Referring now to FIG. 5, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 10 and cloud computing environment 50 can communicate with any type of computerized device over any type of network and/or network addressable connection (e.g., using a web browser).

Figure 6:
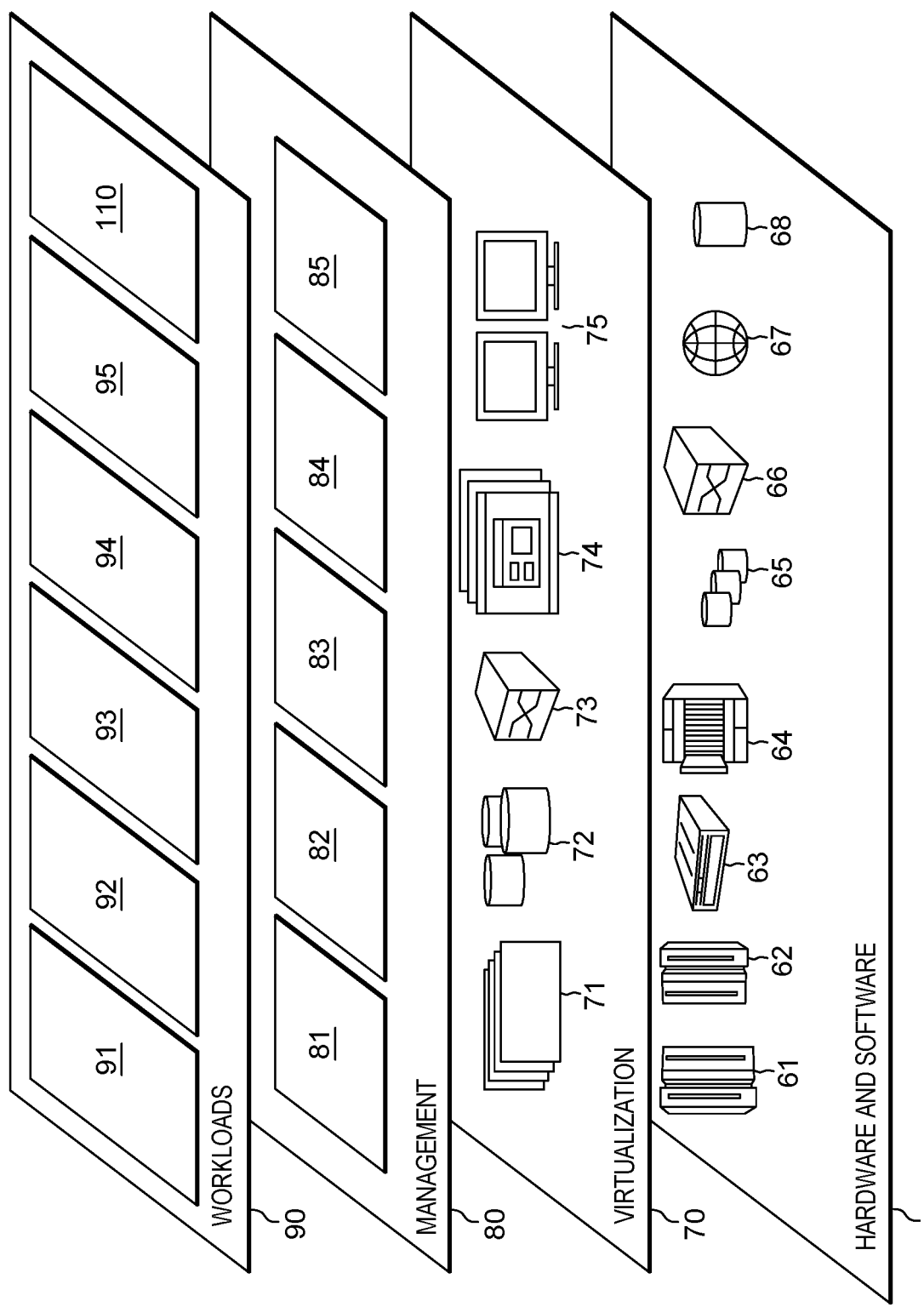
FIG. 6 depicts abstraction model layers in accordance with an embodiment of the present invention.

Referring now to FIG. 6, a set of functional abstraction layers provided by cloud computing environment 50 (FIG. 5) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and haptic analytic interface 110.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for generating preflex stimulation, the method comprising:
    monitoring, by one or more computer processors, one or more sensing devices for data associated with a user activity performed by a user;
    based, at least in part, on the data associated with the user activity, predicting, by the one or more computer processors, a user reaction associated with the user activity;
    transmitting, by the one or more computer processors, a preflex stimulus to at least one muscle of the user, wherein the at least one muscle is associated with the user reaction;
    determining, by the one or more computer processors, a reaction time of the at least one muscle to the preflex stimulus;
    determining, by the one or more computer processors, whether the determined reaction time of the at least one muscle to the preflex stimulus indicates overstimulation; and
    responsive to determining the determined reaction time of the at least one muscle to the preflex stimulus indicates overstimulation, modifying, by the one or more computer processors, the preflex stimulus.

2. The method of claim 1, wherein determining whether the determined reaction time of the at least one muscle to the preflex stimulus indicates overstimulation further comprises determining, by the one or more computer processors, whether the determined reaction time has increased over a previous reaction time.

3. The method of claim 1, further comprising:
    receiving, by the one or more computer processors, data associated with the user activity from the one or more sensing devices;
    receiving, by the one or more computer processors, data associated with the transmitted preflex stimulus;
    based, at least in part, on the received data associated with the user activity from the one or more sensing devices and the received data associated with the transmitted preflex stimulus, determining, by the one or more computer processors, whether the user is in a pressure situation; and
    responsive to determining the user is in a pressure situation, prioritizing, by the one or more computer processors, one or more preflex stimuli.

4. The method of claim 3, wherein prioritizing the one or more preflex stimuli comprises using, by the one or more computer processors, a multi-objective optimization algorithm.

5. The method of claim 3, wherein determining whether the user is in the pressure situation further comprises:
    determining, by the one or more computer processors, whether data associated with a previous user activity is available;
    responsive to determining data associated with a previous user activity is available, comparing, by the one or more computer processors, the data associated with the user activity from the one or more sensing devices and the data associated with the transmitted preflex stimulus to the data associated with a previous user activity; and
    combining, by the one or more computer processors, the data associated with the previous user activity with the data associated with the user activity from the one or more sensing devices and the data associated with the transmitted preflex stimulus to the data associated with a previous user activity.

6. The method of claim 1, wherein predicting a user reaction associated with the user activity includes at least one of a time at which the user is required to react, a duration of time after which the user is required to react, and a location at which the user is required to react.

7. A computer program product for generating preflex stimulation, the computer program product comprising:
    one or more computer readable storage devices and program instructions stored on the one or more computer readable storage devices, the stored program instructions comprising:
    program instructions to monitor one or more sensing devices for data associated with a user activity performed by a user;
    based, at least in part, on the data associated with the user activity, program instructions to predict a user reaction associated with the user activity;
    program instructions to transmit a preflex stimulus to at least one muscle of the user, wherein the at least one muscle is associated with the user reaction;

program instructions to determine a reaction time of the at least one muscle to the preflex stimulus;
program instructions to determine whether the determined reaction time of the at least one muscle to the preflex stimulus indicates overstimulation; and
responsive to determining the determined reaction time of the at least one muscle to the preflex stimulus indicates overstimulation, program instructions to modify the preflex stimulus.

8. The computer program product of claim 7, wherein the program instructions to determine whether the determined reaction time of the at least one muscle to the preflex stimulus indicates overstimulation comprise program instructions to determine whether the determined reaction time has increased over a previous reaction time.

9. The computer program product of claim 7, the stored program instructions further comprising:
program instructions to receive data associated with the user activity from the one or more sensing devices;
program instructions to receive data associated with the transmitted preflex stimulus;
based, at least in part, on the received data associated with the user activity from the one or more sensing devices and the received data associated with the transmitted preflex stimulus, program instructions to determine whether the user is in a pressure situation; and
responsive to determining the user is in a pressure situation, program instructions to prioritize one or more preflex stimuli.

10. The computer program product of claim 9, wherein the program instructions to prioritize the one or more preflex stimuli comprise program instructions to use a multi-objective optimization algorithm.

11. The computer program product of claim 9, wherein the program instructions to determine whether the user is in the pressure situation comprise:
program instructions to determine whether data associated with a previous user activity is available;
responsive to determining data associated with a previous user activity is available, program instructions to compare the data associated with the user activity from the one or more sensing devices and the data associated with the transmitted preflex stimulus to the data associated with a previous user activity; and
program instructions to combine the data associated with the previous user activity with the data associated with the user activity from the one or more sensing devices and the data associated with the transmitted preflex stimulus to the data associated with a previous user activity.

12. The computer program product of claim 7, wherein the program instructions to predict a user reaction associated with the user activity include at least one of a time at which the user is required to react, a duration of time after which the user is required to react, and a location at which the user is required to react.

13. A computer system for generating preflex stimulation, the computer system comprising:
one or more computer processors;
one or more computer readable storage devices;
program instructions stored on the one or more computer readable storage devices for execution by at least one of the one or more computer processors, the stored program instructions comprising:
program instructions to monitor one or more sensing devices for data associated with a user activity performed by a user;
based, at least in part, on the data associated with the user activity, program instructions to predict a user reaction associated with the user activity;
program instructions to transmit a preflex stimulus to at least one muscle of the user, wherein the at least one muscle is associated with the user reaction;
program instructions to determine a reaction time of the at least one muscle to the preflex stimulus;
program instructions to determine whether the determined reaction time of the at least one muscle to the preflex stimulus indicates overstimulation; and
responsive to determining the determined reaction time of the at least one muscle to the preflex stimulus indicates overstimulation, program instructions to modify the preflex stimulus.

14. The computer system of claim 13, wherein the program instructions to determine whether the determined reaction time of the at least one muscle to the preflex stimulus indicates overstimulation comprise program instructions to determine whether the determined reaction time has increased over a previous reaction time.

15. The computer system of claim 13, the stored program instructions further comprising:
program instructions to receive data associated with the user activity from the one or more sensing devices;
program instructions to receive data associated with the transmitted preflex stimulus;
based, at least in part, on the received data associated with the user activity from the one or more sensing devices and the received data associated with the transmitted preflex stimulus, program instructions to determine whether the user is in a pressure situation; and
responsive to determining the user is in a pressure situation, program instructions to prioritize one or more preflex stimuli.

16. The computer system of claim 15, wherein the program instructions to prioritize the one or more preflex stimuli comprise program instructions to use a multi-objective optimization algorithm.

17. The computer system of claim 13, wherein the program instructions to predict a user reaction associated with the user activity include at least one of a time at which the user is required to react, a duration of time after which the user is required to react, and a location at which the user is required to react.

* * * * *